United States Patent [19]
Lengyel

[11] Patent Number: 5,336,161
[45] Date of Patent: Aug. 9, 1994

[54] KNEE ORTHESIS

[75] Inventor: Gabor Lengyel, Altensteig, Fed. Rep. of Germany

[73] Assignee: Biedermann Motech GmbH, VS-Schwenningen, Fed. Rep. of Germany

[21] Appl. No.: 983,417

[22] Filed: Nov. 30, 1992

[30] Foreign Application Priority Data

Dec. 9, 1991 [DE] Fed. Rep. of Germany ....... 4140554

[51] Int. Cl.$^5$ .............................................. A61F 5/00
[52] U.S. Cl. .......................................... 602/26; 602/16
[58] Field of Search ............................... 602/5, 16, 26

[56] References Cited

U.S. PATENT DOCUMENTS

| | | |
|---|---|---|
| 3,581,741 | 6/1971 | Rosman . |
| 4,506,661 | 3/1985 | Foster ................................. 602/26 |
| 4,632,098 | 12/1986 | Grundei et al. ..................... 602/26 |
| 4,686,969 | 8/1987 | Acott . |
| 4,791,916 | 12/1988 | Paez ................................... 602/26 |
| 4,802,466 | 2/1989 | Meyers et al. ...................... 602/26 |
| 4,805,606 | 2/1989 | McDavid, III ...................... 602/26 |
| 4,986,264 | 1/1991 | Miller . |
| 5,016,621 | 5/1991 | Bender ............................... 602/26 |
| 5,063,916 | 11/1991 | France et al. ...................... 602/26 |
| 5,133,341 | 7/1992 | Singer et al. .................. 602/226 X |

FOREIGN PATENT DOCUMENTS 4013693  8/1991  Fed. Rep. of Germany .
WO90/09157  8/1990  PCT Int'l Appl. .

*Primary Examiner*—Richard J. Apley
*Assistant Examiner*—Linda C. M. Dvorak
*Attorney, Agent, or Firm*—Donald Brown

[57] ABSTRACT

A knee orthesis comprises a thigh attachment part, a lower leg attachment part and a joint hingedly connecting both parts, In order to improve the wearing characteristics the knee orthesis comprises a diagonal strut which connects an outer upper point of the thigh attachment part to an inner lower point of the thigh attachment part by extending around the front side of the thigh.

10 Claims, 2 Drawing Sheets

KNEE ORTHESIS

BACKGROUND OF THE INVENTION

The invention relates to a knee orthesis. Such a knee orthesis typically comprises a thigh attachment part, a lower leg attachment part and a joint hingedly connecting both parts. The joint has joint members which are connected to first struts of the thigh attachment part. A strap retainer is provided for connecting the struts of the thigh attachment part.

Such a knee orthesis is disclosed in the German patent application 40 13 693. This known knee orthesis comprises a loop or sling which extends in diagonal direction from the outer side of the thigh retainer belt over the front around the leg in the shape of an 8. The U.S. Pat. No. 4,986,264 discloses a knee orthesis having a shell-type member which is provided at the front side of the lower leg and has a substantially V-shape with a foot portion contacting the region below the knee. The free ends of the shell-type member are connected to struts for the thigh by means of rivets. The EP-A-0 297 766 discloses a knee orthesis wherein the upper member has a plate which embraces the front of the thigh and has strap retainers for attaching the upper and lower end thereof to the thigh. A corresponding plate is provided at the lower part and this plate can also be attached to the lower leg by means of strap retainers in the upper and lower region thereof. The outer sides of both plates are connected with struts which are themselves connected with an inner and outer part of the joint.

OBJECTS OF THE INVENTION

It is an object of the invention to provide an improved knee orthesis in which the above-mentioned drawbacks are avoided. It is a further object of the invention to provide a knee orthesis having an extraordinary adaptability and adjustability. It is a still further object of the invention to provide a knee orthesis which has improved wearing comfort.

SUMMARY OF THE INVENTION

In order to achieve the above-mentioned objects the invention provides a knee orthesis comprising a thigh attachment part having a first strut at a first si de, a second strut at a second side and a strap retainer connecting said first and second struts for attachment to the thigh, a lower leg attachment part having a first leg member at said first side and a second leg member at said second side, a joint means providing a hinged connection of said thigh attachment part and said lower leg attachment part, said joint means having a first joint member hingedly connecting said first strut to said first leg member and a second joint member hingedly connecting said second strut to said second leg member, and a diagonal strut connecting said first and second struts and extending from a first point on one of said struts to a second point on the other of said struts, said second point being closer to said joint than said first point.

BRIEF DESCRIPTION OF THE DRAWINGS

Further features and advantages of the invention result from the description of an embodiment with reference to the figures. In the figures.

DESCRIPTION OF A PREFERRED EMBODIMENT

Figure 1:
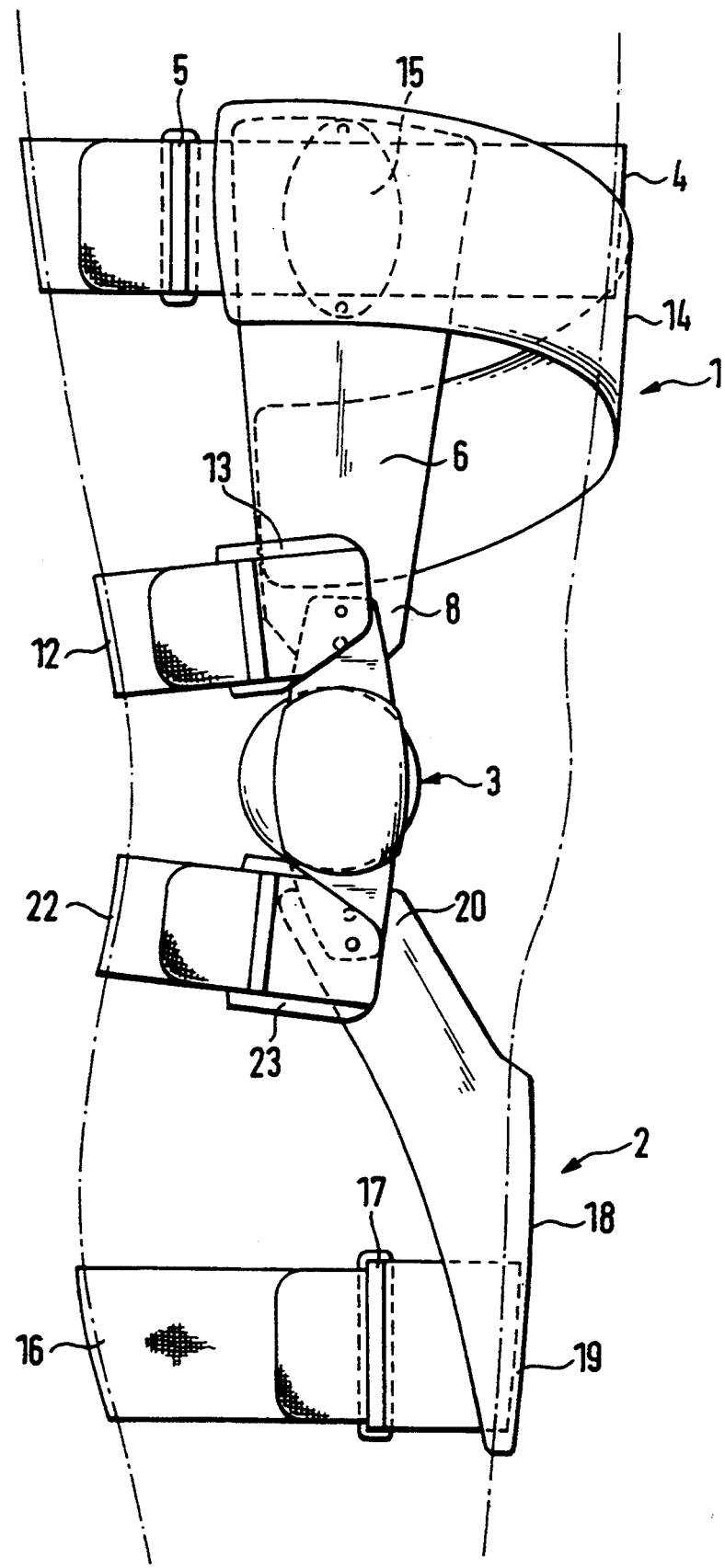
FIG. 1 is a side view of the knee orthesis.
Figure 2:
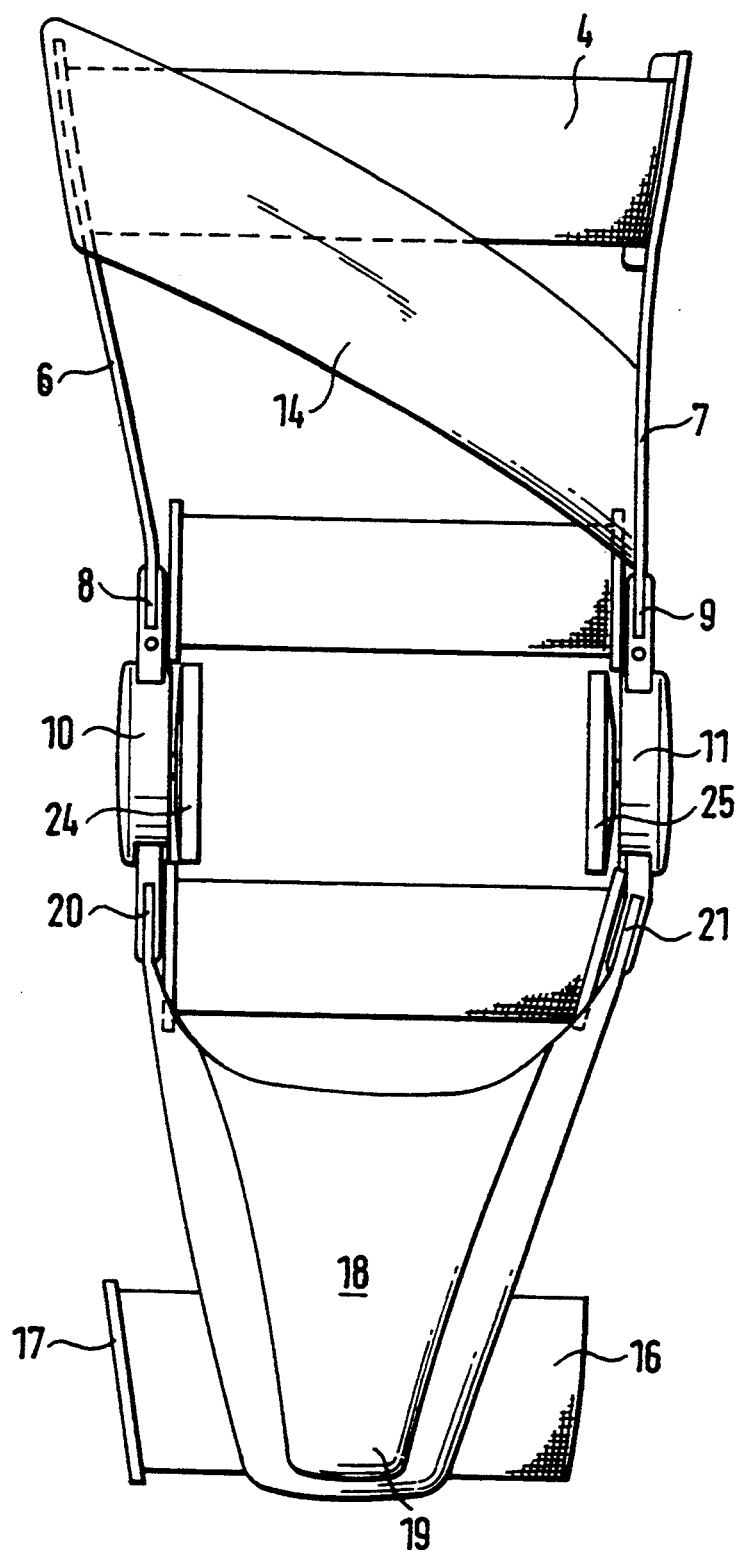
FIG. 2 is a front view of the knee orthesis.

The knee orthesis consists of the thigh attachment part 1, the lower leg attachment part 2 and the joint 3 which connects both parts in a hinged manner.

The upper end of the thigh attachment part 1 is provided with a strap retainer 4 which is formed as a band embracing the thigh and comprising a buckle 5. The strap retainer is fixedly connected with an outer strut 6 and an inner strut 7 at the outer side and inner side, resp. The lower ends 8, 9 of the two struts 6, 7 are connected to a leg of the outer joint member 10 and the inner joint member 11, resp., which together form the joint 3. The thigh attachment part further comprises a second strap retainer 12 at the lower portion of the struts. This strap retainer is fixedly connected to one of the two struts and has a tightening buckle 13 at the other strut for tightening the strap retainer on the back of the thigh above the hollow of the knee.

Further, a thigh diagonal strut 14 is provided which is rigidly connected to the inner strut 7 just above the inner joint member. The diagonal strut 14 extends forward and diagonally upward from this lower mounting point to an upper mounting point 15 which is located substantially vertically above the center of rotation of the outer joint member. The inner side of the diagonal strut and the mounting point of the first strap retainer have cooperating VELCRO-fastening members so that the diagonal strut 14 can be tightly put across the front part of the thigh.

The lower leg attachment part has a third strap retainer 16 at the lower edge thereof which may be put around the lower leg attachment part and can be tightened by means of a buckle 17. The third strap retainer 16 has the front portion thereof rigidly connected to a lower leg form member 18 which is formed as a V-shaped shell which is adapted to the usual form of the lower leg below the knee and has the foot portion 19 thereof connected to the third strap retainer. The free ends 20, 21 of the lower leg form member 18 are rigidly connected to the second legs of the two joint members 10 and 11, resp. The free ends 20, 21 are also connected to the ends of a fourth strap retainer 22 which has one end thereof connected to a free end 21 of the lower leg form member and the other free end thereof connected to the other free end of the lower leg form member 18 through a buckle 23. The lower leg form member 18 can be smoothly put on the lower leg by means of the third and fourth strap retainer and the corresponding buckles.

In the usual manner the two joint members 10, 11 have respective pressure cushions 24, 25 at the inner sides thereof for abutting the sides of the knee.

The strap retainers are preferably manufactured from a tissue or woven cloth which ensures that the retainers are well tolerable and sufficiently strong. The outer strut, the diagonal strut and the lower leg form member are manufactured from a thermoplastic material with or without fi bet reinforcement such as glass fiber, carbon fiber or aramite fiber or from light metals such as titanium and aluminum or alloys thereof. It is important that these materials exhibit a high stability and a low weight and that they are reformable and corrosion-resistant.

In the above embodiment the thigh diagonal strut 14 is mounted to the inner strut slightly above the inner joint member, while the upper mounting point 15 is on the exterior side. Although this embodiment is particularly preferred, it is also possible according to a further embodiment to extend the thigh diagonal strut to an upper mounting point which is substantially vertically above the center of rotation of the inner joint member, while the diagonal strut is mounted to the outer strut slightly above the outer joint member.

Although the invention has been described with reference to a specific example embodiment, it is to be understood that it is intended to cover all modifications and equivalents within the scope of the appended claims.

What is claimed is:

1. A knee orthesis comprising
    a thigh attachment part (1) having a first strut (6) at a first side, a second strut (7) at a second side and a first strap retainer (4) connecting said first and second struts for attachment to the thigh,
    a lower leg attachment part (2) having a first free end (20) at said first side and a second free end (21) at said second side,
    a joint means (3) providing a hinged connection of said thigh attachment part (1) and said lower leg attachment part (2), said joint means (3) having a first joint member (10) hingedly connecting said first strut (6) to said first free end (20) and a second joint member (11) hingedly connecting said second strut (7) to said second free end (21) and
    rigid diagonal strut (14) connecting said first and second struts (6,7) and extending from a first point (15) on one of said struts to a second point on the other of said struts, said second point being closer to said joint means (3) than said first point (15).

2. The knee orthesis of claim 1, wherein said first side is the outer side and said second side is the inner side.

3. The knee orthesis of claim 1, wherein said first side is the inner side and said second side is the outer side.

4. The knee orthesis of claim 1 wherein said thigh attachment part (1) comprises a second strap retainer (12), which is connected to said first strut (6) and said second strut (7) for connecting said second strap retainer (12) with said first joint member (10) and said second joint member (11), respectively.

5. The knee orthesis of claim 1, wherein said lower leg attachment part (2) comprises a third strap retainer (16) and a shell-shaped member (18), which comprises said first and said second free end (20, 21), connecting said lower strap retainer (16) to said first and second joint members (10, 11).

6. The knee orthesis of claim 5, wherein said lower leg attachment part (2) comprises a fourth strap retainer (22), which is connected to said first and said second free end, respectively.

7. The knee orthesis of claim 1, wherein said first and said second joint member (10, 11) each comprise a first leg to which said first free end (2) and said second free end (21) is connected, respectively.

8. The knee orthesis of claim 1, wherein said first and said second joint member (10, 11) each comprise a second leg to which said first free end (20) and said second free end (21) is connected, respectively.

9. The knee orthesis joint of claim 1, wherein said diagonal strut is formed of a thermoplastic material with or without fiber reinforcement comprising glass fiber, carbon fiber or aramite fiber or of light metals titanium and aluminum or alloys thereof.

10. The knee orthesis joint of claim 1, wherein said shell-shaped member is formed of a thermoplastic material with or without fiber reinforcement comprising glass fiber, carbon fiber or aramite fiber or of light metals titanium and aluminum or alloys thereof.

* * * * *